United States Patent
Engelbart et al.

(10) Patent No.: US 7,236,625 B2
(45) Date of Patent: Jun. 26, 2007

(54) SYSTEMS AND METHOD FOR IDENTIFYING FOREIGN OBJECTS AND DEBRIS (FOD) AND DEFECTS DURING FABRICATION OF A COMPOSITE STRUCTURE

(75) Inventors: Roger W Engelbart, St. Louis, MO (US); Reed Hannebaum, Mount Vernon, IL (US); Steve Schrader, Bridgeton, MO (US); Scott T Holmes, Oxford, PA (US); Craig Walters, Wentzville, MO (US)

(73) Assignee: The Boeing Company, Chicago, IL (US)

( * ) Notice: Subject to any disclaimer, the term of this patent is extended or adjusted under 35 U.S.C. 154(b) by 428 days.

(21) Appl. No.: 10/846,974

(22) Filed: May 14, 2004

(65) Prior Publication Data

US 2005/0025350 A1   Feb. 3, 2005

Related U.S. Application Data

(63) Continuation of application No. 10/628,691, filed on Jul. 28, 2003, now abandoned.

(51) Int. Cl.
*G06K 9/00* (2006.01)
(52) U.S. Cl. .................. 382/141; 250/306; 348/86; 348/126; 700/108; 438/16; 356/237.1
(58) Field of Classification Search ........ 392/141–152; 250/306; 348/86, 87, 126–134; 700/108–110; 438/16; 356/237.1–237.6

See application file for complete search history.

(56) References Cited

U.S. PATENT DOCUMENTS 3,879,245 A    4/1975   Fetherson et al.

(Continued)

FOREIGN PATENT DOCUMENTS

EP         0 319 797        6/1989

(Continued)

OTHER PUBLICATIONS

Bruckstein et al., "Omniview Cameras With Curved Surface Mirrors", Jun. 12, 2000, IEEE Omnidirectional Vision Proceedings, pp. 79-84.*

(Continued)

*Primary Examiner*—Jingge Wu
*Assistant Examiner*—Aaron Carter
(74) *Attorney, Agent, or Firm*—Harness, Dickey & Pierce, P.L.C.

(57) ABSTRACT

Systems and methods for identifying foreign objects and debris (FOD) and defects during fabrication of a composite structure. The system includes at least one light source positioned to emit light that illuminates a portion of the composite structure with bright field illumination and that also illuminates another portion of the composite structure with dark field illumination. The bright field illumination is reflected differently by defects in the composite structure than from portions of the composite structure that are defect free. The dark field illumination is reflected differently by FOD on the composition structure than from surfaces of the composite structure that are FOD free. The system also includes at least one camera for receiving images of the illuminated portions of the composite structure. The images received by the camera may be processed by a processor which then outputs a response identifying defects and foreign objects and debris based on the images.

33 Claims, 8 Drawing Sheets

U.S. PATENT DOCUMENTS

| | | | |
|---|---|---|---|
| 4,064,534 | A | 12/1977 | Chen et al. |
| 4,310,132 | A | 1/1982 | Robinson et al. |
| 4,548,859 | A | 10/1985 | Kline et al. |
| 4,608,220 | A | 8/1986 | Caldwell et al. |
| 4,693,678 | A | 9/1987 | Von Volkli |
| 4,699,683 | A | 10/1987 | McCowin |
| 4,760,444 | A | 7/1988 | Nielson et al. |
| 4,780,262 | A | 10/1988 | Von Volkli |
| 4,790,898 | A | 12/1988 | Woods |
| 4,830,298 | A | 5/1989 | Van Blunk |
| 4,877,471 | A | 10/1989 | McCowin et al. |
| 4,941,182 | A | 7/1990 | Patel |
| 5,024,399 | A | 6/1991 | Barquet et al. |
| 5,058,497 | A | 10/1991 | Bishop et al. |
| 5,153,668 | A * | 10/1992 | Katzir et al. .............. 356/237.2 |
| 5,198,983 | A | 3/1993 | Blake et al. |
| 5,337,647 | A | 8/1994 | Roberts et al. |
| 5,439,549 | A | 8/1995 | Fryc et al. |
| 5,450,147 | A | 9/1995 | Dorsey-Palmateer |
| 5,518,208 | A | 5/1996 | Roseburg |
| 5,540,126 | A | 7/1996 | Piramoon |
| 5,562,788 | A | 10/1996 | Kitson et al. |
| 5,651,600 | A | 7/1997 | Dorsey-Palmateer |
| 5,683,646 | A | 11/1997 | Reiling, Jr. |
| 5,700,337 | A | 12/1997 | Jacobs et al. |
| 5,746,553 | A | 5/1998 | Engwall |
| 5,804,276 | A | 9/1998 | Jacobs et al. |
| 5,814,386 | A | 9/1998 | Vasiliev et al. |
| 5,822,055 | A * | 10/1998 | Tsai et al. ................. 356/237.1 |
| 5,825,495 | A | 10/1998 | Huber |
| 5,871,117 | A | 2/1999 | Protasov et al. |
| 5,917,588 | A * | 6/1999 | Addiego ................... 356/237.2 |
| 5,949,901 | A * | 9/1999 | Nichani et al. .............. 382/149 |
| 5,963,660 | A | 10/1999 | Koontz et al. |
| 5,979,531 | A | 11/1999 | Barr et al. |
| 6,012,883 | A | 1/2000 | Engwall et al. |
| 6,013,341 | A | 1/2000 | Medvedev et al. |
| 6,045,651 | A | 4/2000 | Kline et al. |
| 6,074,716 | A | 6/2000 | Tsotsis |
| 6,075,883 | A * | 6/2000 | Stern et al. .................. 382/144 |
| 6,086,696 | A | 7/2000 | Gallagher |
| 6,106,649 | A | 8/2000 | Slyne |
| 6,112,792 | A | 9/2000 | Barr et al. |
| 6,168,358 | B1 | 1/2001 | Engwall et al. |
| 6,205,239 | B1 | 3/2001 | Lin et al. |
| 6,288,780 | B1 * | 9/2001 | Fairley et al. ............ 356/237.1 |
| 6,364,250 | B1 | 4/2002 | Brinck et al. |
| 6,369,492 | B1 | 4/2002 | Sugimoto |
| 6,390,169 | B1 | 5/2002 | Johnson |
| 6,451,152 | B1 | 9/2002 | Holmes et al. |
| 6,480,271 | B1 | 11/2002 | Cloud et al. |
| 6,648,273 | B2 | 11/2003 | Anast |
| 6,692,681 | B1 | 2/2004 | Lunde |
| 6,725,123 | B1 | 4/2004 | Denuell |
| 6,799,619 | B2 | 10/2004 | Holmes et al. |
| 6,937,753 | B1 * | 8/2005 | O'Dell et al. ................ 382/141 |
| 2001/0002246 | A1 | 5/2001 | Vaez-Iravani et al. |
| 2001/0023349 | A1 | 9/2001 | Van Tassel et al. |
| 2002/0141632 | A1 | 10/2002 | Engelbart et al. |
| 2005/0030527 | A1 * | 2/2005 | Reinhorn ................. 356/237.1 |

FOREIGN PATENT DOCUMENTS

| | | |
|---|---|---|
| EP | 0 833 146 | 4/1998 |
| EP | 0903574 | 3/1999 |
| EP | 1 030 172 | 8/2000 |
| JP | 62001012930 | 1/2001 |
| WO | WO 94/18643 | 8/1994 |
| WO | WO 2004/025385 | 3/2004 |

OTHER PUBLICATIONS

Krupka R; Walz T; Ettemeyer A: "Industrial applications of shearography for inspection of aircraft components" Proceedings of the 8th European Conference of Nondestructive Testing, Barcelona (Spain), Jun. 17-21, 2002, 'Online! Jun. 30, 2002, XP0023531899 NDT.NET—Feb. 2003, vol. 8, No. 2 Retrieved fromt the Internet: URL:http://www.ndt.net/article/ecndt02/484/484.htm> 'retrieved on Oct. 31, 2005!.

Prof. J. Zhang: "Angewandte Sensorik" CH. 4, Sensoren in der Robotik, Nov. 11, 2003, pp. 76-113, XP002327793; URL:http://tech-www.informatik.uni-hamburg.de/lehre/ws2003/volesungen/angewandte_sensorik/volesung_03.pdf>, retrieved on Apr. 2004, p. 89.

European Search Report, Application No. 04076900.2, dated Dec. 1, 2004, 4 pages.

Patent Abstracts of Japan, vol. 2000, No. 16, May 8, 2001, Japan.

U.S. Appl. No. 60/559,911, filed Apr. 6, 2004, Johnson et al.

US.Appl. No. 60/559,890, filed Apr. 6, 2004, Biornstad et al.

US.Appl. No. 10/819,084, filed Apr. 6, 2004, Turnmire et al.

US.Appl. No. 10/853,075, filed May 25, 2004, Johnson et al.

US.Appl. No. 10/949,848, filed Sep. 23, 2004, Johnson et al.

Advaned Technology Tape Laying for Affordable Manufacturing of Large Composite Structures; http://www.cinmach.com/tech/pdf/TapeLayingGrimshaw.pdf; Michael N. Grimshaw, et al; 11 pages.

Fiber Placement; http://www.cinmach.com/tech/pdf/asm_chapter_fp.pdf; Don O. Evans; Cincinnati Machine; 3 pages.

Automated Tape Laying; http://www.cinmach.com/tech/pdf/Grimshaw%20ASM%20Handbook.pdf; Michael N. Grimshaw; Cincinnati Machine; 6 pages.

Raytheon Aircraft's Hawker Horizon Reaches Fuselage Milestone, Raytheon News Release; http://www.beechcraft.de/Presse/2000/100900b.htm; 2 pages.

Pending U.S. Appl. No. 10/851,381 entitled composite Barrel Sections for Aircraft Fuselages and Other Structures, and Methods and Systems for Manufacturing Such Barrel Sections, filed May, 20, 2004, Biornstad.

Fiedler, L., et al, "Tango Composite Fuselage Platform", SAMPE Journal, vol. 39, No. 1, Jan./Feb. 2003, pp. 57-63.

BAe 146, Flight International, May 2, 1981, 2 pages.

A Barrelful of Experience, Intervia, May 1992, 2 pages.

Raytheon, Mar. 2000, vol. 4, No. 2, http://www.cts.com/king/vasci/newsletter/vol42.html.

Business Aviation, Jun. 7, 2002, http://www.aviationnow.com/avnow/news/channel_busav.jsp?view=story&id=news/btoyo0607.xml.

Beechcraft's Composit Challenge, http://www.aerotalk.com/Beech.cfm.

Evans, Don O., "Fiber Placement", 3 pages, Cincinnati Machine, pp. 477-479.

U.S. Appl. 10/068735 entitled Composite Material Collation Machine and Associated Method for High Rate Collation of Composite Materials, filed Feb. 6, 2002, Engelbart et al.

U.S. Appl. No. 10/217,805 entitled System for Identifying Defects in a Composite Structure, filed Aug. 13, 2002, Engelbart et al.

U.S. Appl. No. 10/301,949 entitled Parallel Configuration Composite Material Fabricator, filed Nov. 22, 2002, Nelson.

U.S. Appl. No. 10/628,691 entitled Systems and Methods for Identifying Foreign Objects and Debris (FOD) and Defects During Fabrication of a composite Structure, filed Jul. 28, 2003, Engelbart.

U.S. Appl. No. 10/630,594 entitled Composite Fuselage Maching, filed Jul. 23, 2003, Braun.

U.S. Appl. No. 10/646,316 entitled Unidirectional Multihead Fiber Placement, filed Aug. 22, 2003, New.

U.S. Appl. No. 10/646,392 entitled Automated Composite Lay-Up to an Internal Fuselage Mandrel, filed Aug. 22, 2003, Engwall.

U.S. Appl. No. 10/646,509 entitled Multiple Head Automated Composite Laminating Machine for the Fabrication of Large Barrel Section Components, filed Aug. 22, 2003, Johnson.

U.S. Appl. No. 10/664,148 entitled Composite Material Collation Machine and Associated Method for High Rate Collation of Composite Materials; divisional application of 10/068,735, filed Sep. 17, 2003, Engelbart, et al.

U.S. Appl. No. 10/717,030 entitled Method of Transferring Large Uncured Composite Lamintes, filed Nov. 18, 2003, Johnson.

U.S. Appl. No. 10/726,099 entitled Systems and Methods for Determining Defect Characteristics of a Composite Structure, filed Dec. 2, 2003, Engelbart et al.

U.S. Appl. No. 10/799,306 entitled Systems and Methods for Enabling Automated Return to and/or Repair of Defects with a Material Placement Machine, filed Mar. 12, 2004, Engelbart et al.

U.S. Appl. No. 10/822,538 entitled Systems and Methods for Using Light to Indicate Defect Locations on a Composite Structure, filedMar. 12, 2004, Engelbart et al.

Sharp et al.; "*Material Selection/Fabrication Issues for Thermoplastic Fiber Placement*", Journal of Thermoplastic Composite Materials, vol. 8; Jan. 1995, p. 2-14.

http://www.cinmach.com/WolfTracks4_1/MTG_WT7.htm; Premier 1 Features Lighter, Stronger All-Composite Fuselage, 3 pages.

http://www.cinmach.com/compnews/PressReleases/pr00-11.htm; Raytheon Aircraft Orders Four More Fiber Cincinnati Fiber Placement Systems for Industry's First Composite-Fuselage Business Jets, 2 pages.

http://www.rockymountaincomposites.com/wind_sys.htm; Filament Winding, 2 pages.

\* cited by examiner

SYSTEMS AND METHOD FOR IDENTIFYING FOREIGN OBJECTS AND DEBRIS (FOD) AND DEFECTS DURING FABRICATION OF A COMPOSITE STRUCTURE

CROSS-REFERENCE TO RELATED APPLICATION

This application is a continuation of U.S. patent application Ser. No. 10/628,691, filed on Jul. 28, 2003 now abandoned. The entire disclosure of which is incorporated herein by reference.

COPYRIGHT NOTICE

A portion of the disclosure of this document contains material that is subject to copyright protection. The copyright owner has no objection to the facsimile reproduction by anyone of the patent disclosure, as it appears in the U.S. Patent and Trademark Office patent files or records, but otherwise the copyright owner reserves all copyright rights whatsoever.

FIELD

The present invention relates generally to the fabrication of composite structures, and more particularly to systems and methods for locating foreign objects and debris (FOD) and defects during fabrication of a composite structure.

BACKGROUND

Composite structures have been known in the art for many years. Although composite structures can be formed in many different manners, one advantageous technique for forming composite structures is a fiber placement or automated collation process. According to conventional automated collation techniques, one or more ribbons of composite material (also known as composite strands or tows) are laid down on a substrate. The substrate may be a tool or mandrel, but, more conventionally, is formed of one or more underlying layers of composite material that have been previously laid down and compacted.

Conventional fiber placement processes utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. To complete the part, additional strips of composite material can be applied in a side-by-side manner to each layer and can be subjected to localized heat and pressure during the consolidation process.

Unfortunately, defects can occur during the placement of the composite strips onto the underlying composite structure. Such defects can include tow gaps, overlaps, dropped tows, puckers, and twists. Additionally, foreign objects and debris (FOD), such as resin balls and fuzz balls, can accumulate on a surface of the composite structure. Resin balls are small pieces of neat resin that build up on the surfaces of the fiber placement head as the pre-impregnated tows pass through the guides and cutters. The resin balls become dislodged due to the motion and vibration of the fiber placement machine, and drop on to the surface of the ply. If not removed, subsequent courses will cover the resin ball and create a bump in the laminate whereat there may be no compaction of the tows. Fuzz balls are formed when fibers fray at the edges of the tows and then break off as the tows are passed through the cutter assembly. The broken fibers collect in small clumps that fall onto the laminate and, if not removed, are covered by the next course.

Composite laminates fabricated by fiber placement processes are typically subjected to a 100% ply-by-ply visual inspection for both defects and FOD. Typically, these inspections are performed manually during which time the fiber placement machine is stopped and the process of laying materials halted until the inspection and subsequent repairs, if any, are completed. In the meantime, the fabrication process has been disadvantageously slowed by the manual inspection process and machine downtime associated therewith.

SUMMARY

The inventors hereof have succeeded in designing systems and methods for identifying foreign objects and debris (FOD) and defects during fabrication of a composite structure. In one embodiment, the system includes at least one light source positioned to emit light that illuminates a portion of the composite structure with bright field illumination and that also illuminates another portion of the composite structure with dark field illumination. The bright field illumination is reflected differently by defects in the composite structure than from portions of the composite structure that are defect free. The dark field illumination is reflected differently by FOD on the composition structure than from surfaces of the composite structure that are FOD free. The system also includes at least one camera for receiving images of the illuminated portions of the composite structure.

Further areas of applicability of the present invention will become apparent from the detailed description provided hereinafter. It should be understood that the detailed description and specific examples, while indicating at least one exemplary embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Corresponding reference characters indicate corresponding features throughout the several views of the drawings.

DETAILED DESCRIPTION OF THE EXEMPLARY EMBODIMENTS

Figure 1:
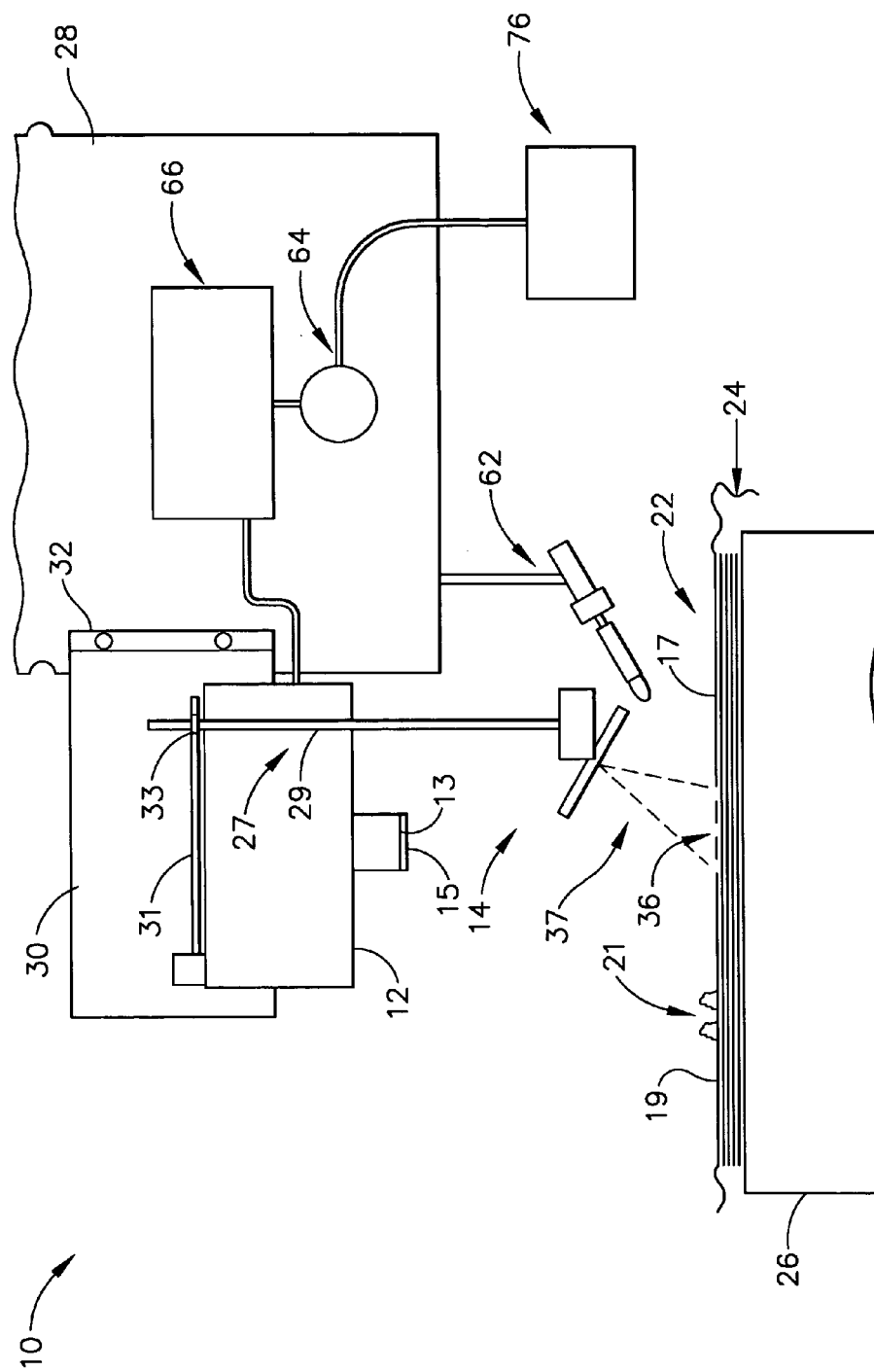
FIG. 1 is a schematic view of a system for identifying FOD and defects during fabrication of a composite structure according to one embodiment of the present invention.
Figure 2:
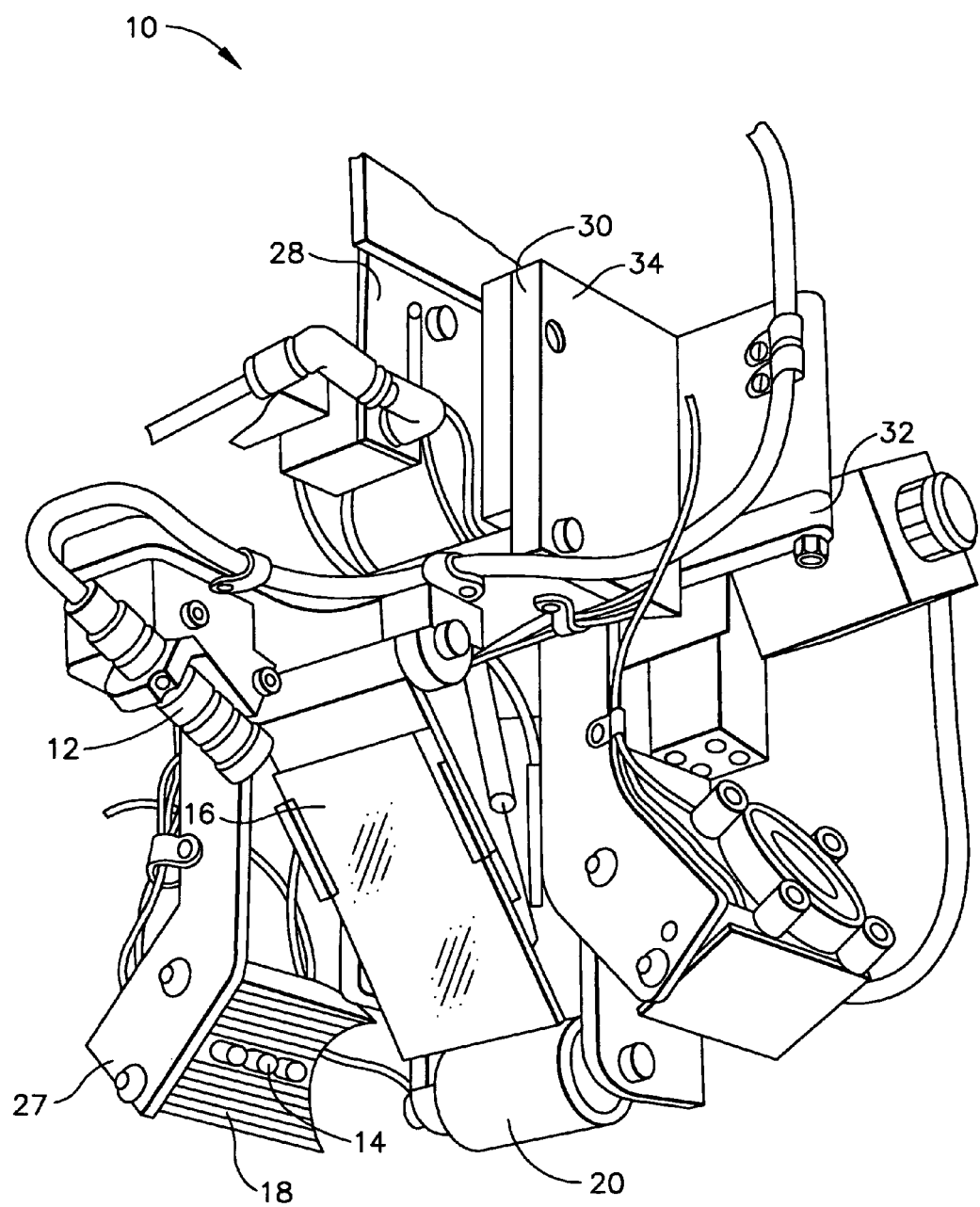
FIG. 2 is a perspective view of a system for identifying FOD and defects during fabrication of a composite structure according to another embodiment of the present invention.
Figure 4:
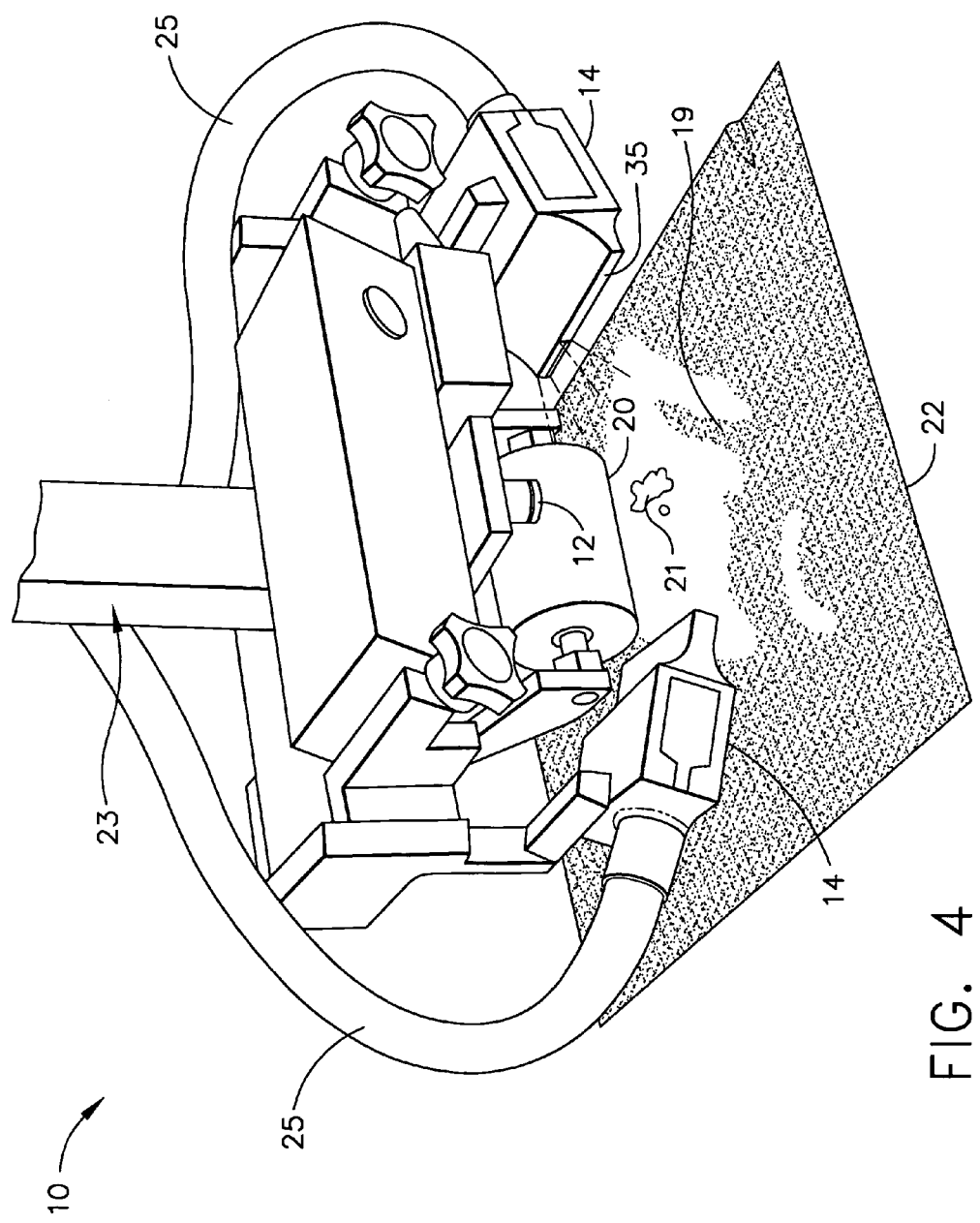
FIG. 4 is a perspective view of a system for identifying FOD and defects during fabrication of a composite structure according to another embodiment of the present invention.

Embodiments of systems for identifying foreign objects and debris (FOD) and defects during fabrication of a composite structure are generally indicated by reference numeral 10 in FIGS. 1, 2 and 4. As shown in FIG. 1, the system 10 is positioned proximate a composite structure 22, which is generally comprised of a plurality of adjacent tows or strips 24 of composite tape. The strips 24 typically include a plurality of fibers embedded in a resin or other material that becomes tacky or flowable upon the application of heat. The strips 24 are arranged on a work surface, such as a table, mandrel, or other tool 26, and compacted with a compaction roller 20 (FIG. 2) to form the composite structure 22 according to an automated collation technique, such as that described in U.S. patent application Ser. No. 10/068,735, filed on Feb. 6, 2002, entitled "Composite Material Collation Machine and Associated Method for High Rate Collation of Composite Materials." The contents of U.S. patent application Ser. No. 10/068,735 is incorporated herein by reference in its entirety as if fully set forth herein.

With further reference to FIG. 1, the system 10 includes at least one camera 12 and at least one light source 14. The camera 12 is connected to a processor 66 for interpreting the images the camera 12 captures, or to a storage device 64 for storing the images, or both, as discussed more fully below.

The light source 14 is positioned to emit light that illuminates a first portion 17 of the composite structure 22 with bright field illumination (also known as incident light) while also illuminating a second portion 19 with dark field illumination (also known as indirect light). More specifically, the bright field illumination "spills" over onto the second portion 19 of the composite structure 22 and illuminates the second portion 19 with dark field illumination.

The bright field illumination is reflected differently by defects in the composite structure than from portions of the composite structure that are defect free. For example, the bright field illumination reflecting off non-defective portions of the composite structure 22, and light that fails to reflect off of defects in the composite structure 22, or vice versa, creates visible images that can be captured by the camera 12. Details regarding systems and methods for identifying defects in a composite structure during fabrication thereof are included in U.S. patent application Ser. No. 09/819,922, filed on Mar. 28, 2001, entitled "System and Method for Identifying Defects in a Composite Structure" and in U.S. patent application Ser. No. 10/217,805, filed on Aug. 13, 2002, entitled "System for Identifying Defects in a Composite Structure". The contents of U.S. patent application Ser. Nos. 09/819,922 and 10/217,805 are incorporated herein by reference as if fully set forth herein.

In addition, the dark field illumination is reflected differently by FOD on the composition structure 22 than from surfaces of the composite structure that are FOD free. For example, the dark field illumination reflecting off FOD, such as resin balls and fuzz balls, on the composite structure 22, and the dark field illumination that fails to reflect off the FOD-free portions of the composite structure 22, or vice versa, creates visible images that can also be captured by the camera 12, as discussed in detail below.

As shown in FIG. 1, the camera 12 is positioned near the composite structure 22 so as to capture images of the illuminated portions 17 and 19 of the composite structure 22, which are typically immediately downstream of the nip point at which a composite tow is joined with the underlying structure. Alternatively, and as shown in FIG. 2, a reflective surface 16 may be positioned near the composite structure (not shown in FIG. 2), and angled such that the reflective surface 16 reflects an image of the illuminated portions 17 of the composite structure. In one embodiment, the angle of the reflective surface 16 to the composite structure is about sixty-five degrees, but the reflective surface 16 can also be positioned at any appropriate angle in order to reflect images of the illuminated portions of the composite structure to the camera 12. The camera 12 then may be positioned to point toward the reflective surface 16 in order to capture the close-range images of the illuminated portions of the composite structure from the reflective surface 16. More than one reflective surface 16 may also be utilized in further embodiments of the present invention in which the reflective surfaces 16 cooperate in order to direct images of the illuminated portions of the composite structure to the camera 12.

For composite structures having curved/contoured surfaces, an image of the composite structure is advantageously captured from a position as close as possible to the nip point in order to obtain an accurate representation of the composite structure for processing. Thus, the configuration illustrated in FIG. 2 is particularly advantageous for capturing images of curved/contoured surfaces of the composite structure because the reflective surface 16 reflects images of the composite structure for the camera 12 to capture from a position as close as possible to the composite structure. In addition, this configuration permits the camera 12 to be placed further from the composite structure than the reflective surface 16, such that the camera 12 does not obstruct the functionality of other parts of the fiber placement device, or vice versa. Further, the reflective surface 16 can also provide a "square on" view of the area being inspected, which, in turn, can materially improve the ability to dimension the two gaps for pass/fail decisions.

A wide range of cameras can be used including commercially-available cameras capable of acquiring black and white images. In one embodiment, the camera 12 is a television or other type of video camera having an image sensor (not shown) and a lens 13 through which light passes when the camera 12 is in operation. Other types of cameras or image sensors can also be used, such as an infrared-sensitive camera, a visible light camera with infrared-pass filtration, a fiber optic camera, a coaxial camera, Charge Coupled Device (CCD), or Complementary Metal Oxide Sensor (CMOS). The camera 12 can be positioned proximate the composite structure 22 on a stand (not shown) or mounted to a frame 28 or similar device. In embodiments of the present invention that do not include a reflective surface 16, the camera 12 may be positioned approximately six inches from the surface of the composite structure 22, and mounted to the frame 28 by way of a bracket 30 and associated connectors 32, as shown in FIG. 1.

In an embodiment that includes a reflective surface 16, however, the reflective surface 16 may be positioned approximately three inches from the surface of the composite structure 22, and the camera 12, pointed toward the reflective surface 16, may be positioned further away from the composite structure, as described above. In further embodiments of present invention, the reflective surface 16 may be positioned at other distances from the surface of the composite structure 22, such as from one to six inches, to accurately reflect an image of the surface of the composite structure toward the camera 12. Reflective surfaces can also be utilized to allow the camera to be placed in an advantageous position which might otherwise be blocked by portions of the compaction roller 20 (FIG. 2) and/or other parts of the fiber placement system.

The connectors 32 may be rivets, screws or the like that mount the camera 12 to the frame 28 in a stationary position. Alternatively, the connectors 32 may be a hinge-type connector that permits the camera 12, light source 14, and associated assembly to be rotated away from the composite structure 22. This embodiment is advantageous in situations where other parts of the material placement device, particularly the parts located behind the camera 12 and associated assembly, must be accessed, such as for maintenance, cleaning, or the like.

FIG. 2 illustrates an alternative embodiment of the hinge-type connector 32 that mounts the camera 12, reflective surface 16, light source 14, and associated assembly (i.e., camera assembly) to the frame 28 by way of a bracket 30. A suitable fastener, such as a thumbscrew or any other fastener that may be removed or loosened with relative ease, can be inserted through hole 34 and then tightened to secure the camera assembly in place for operation. The fastener may be loosened or removed, for example, to rotate the camera assembly away from the compaction roller 20 and other parts of the fiber placement device.

With further reference to FIG. 1, a filter 15 can be placed on the lens 13 for filtering light in a particular manner. In one embodiment, the filter 15 is designed to filter light such that only the infrared component or a certain infrared wavelength or range of wavelengths of light can pass into the camera 12. Thus, the filter 15 prevents ambient visible light from entering the camera 12 and altering the appearance of the captured image.

Other methods of filtering light can also be used to achieve the same, or at least similar, result. For example, the camera may be designed to include a built-in filter of equivalent optical characteristics. In addition, the filter can be located between the camera lens 13 and image sensor. Alternatively, the camera may include an image sensor that is only sensitive in the infrared spectrum (i.e., an infrared-sensitive camera), thus eliminating the need for the filter.

The light source 14 of the system 10 will now be described in detail. The light source 14 is positioned to emit light that illuminates the first portion 17 of the composite structure 22 with bright field illumination (i.e., incident light) while also illuminating the second portion 19 with dark field illumination (i.e., indirect light). In one embodiment, the bright field illumination "spills" over onto the second portion 19 and thus illuminates the second portion 19 with dark field illumination.

In FIG. 1, the light source 14 is shown positioned at an oblique angle 37 relative to the composite structure 22. The oblique angle 37 may be about forty-five degrees, although other angles are possible depending on the application. In addition, the light source 14 is also shown positioned to emit light in a direction substantially perpendicular to the direction of placement of the strips 24 in order to highlight the defects 36, as described below.

Further, the system 10 may include more than one light source. For example, the embodiment of FIG. 2 includes two light sources 14 positioned relative to the composite structure and compaction roller 20 on either side of the reflective surface 16 and camera 12. Another exemplary embodiment that includes two light sources 14 is shown in FIG. 4 in which two linear optical fiber arrays are positioned on opposed sides of the camera 12.

In FIG. 1, the light source 14 is adjustably positioned relative to the composite structure 22 by mounting or attaching the light source 14 to a mounting apparatus 27. The mounting apparatus 27 can include a main shaft 29, a secondary shaft 31, and a locking clamp 33 for quickly and accurately adjusting the position of the light source 14. The mounting apparatus 27, in turn, can be attached to the frame 28, to the camera 12, to the bracket 30, or to some other object that defines a common position for both the light source 14 and the camera 12 such that the light source 14 and camera 12 maintain a constant spatial relationship relative to one another.

The quality and magnitude of the surface illumination of the composite structure is greatly affected by ambient lighting and by the reflectivity of the material. Accordingly, embodiments of the invention advantageously employ an infrared light source to more effectively illuminate dark flaws on a dark background. In this regard, the light source 14 can be selected from an infrared light or another type of light having an infrared component, such as a halogen light source (FIG. 3) or other incandescent light sources (not shown). In other embodiments, the light source 14 can also include a fluorescent light source (e.g., white light LEDs, low pressure/mercury filled phosphor glass tube, etc.), a strobe or stroboscopic light source, a noble gas arc lamp (e.g., xenon arc, etc.), metal arc lamp (e.g., metal halide, etc.) and a lasers (e.g., pulsed lasers, solid state laser diode arrays, infrared diode laser arrays, etc.). The light from the light source 14 may also be pumped from through optical fibers to the point of delivery, such as is shown in FIG. 4.

In some embodiments, the light source 14 is operated at a power level that maximizes, or at least significantly increases, the infrared (IR) component of the light which works well for inspecting dark tow material, such as carbon. In this regard, exemplary power levels in the range of up to about one hundred fifty watts (150 W) in the wavelength range of about seven hundred nanometers to one thousand nanometers (700 nm–1000 nm) have been sufficient. However, the particular power levels and wavelengths for the light source will likely depend at least in part on the camera's speed and sensitivity, speed at which the material is being laid, delivery losses, and reflectivity of the material being inspected, among other factors. For example, In other embodiments, wavelengths and power levels suitable for inspecting highly reflective materials can be employed.

In the embodiment shown in FIG. 1, the light source 14 may comprise a plurality of LEDs arranged in an array or cluster formation. In one specific embodiment, the light source 14 includes 24 LEDs mounted in an array upon a three-inch square printed circuit board.

Figure 3:
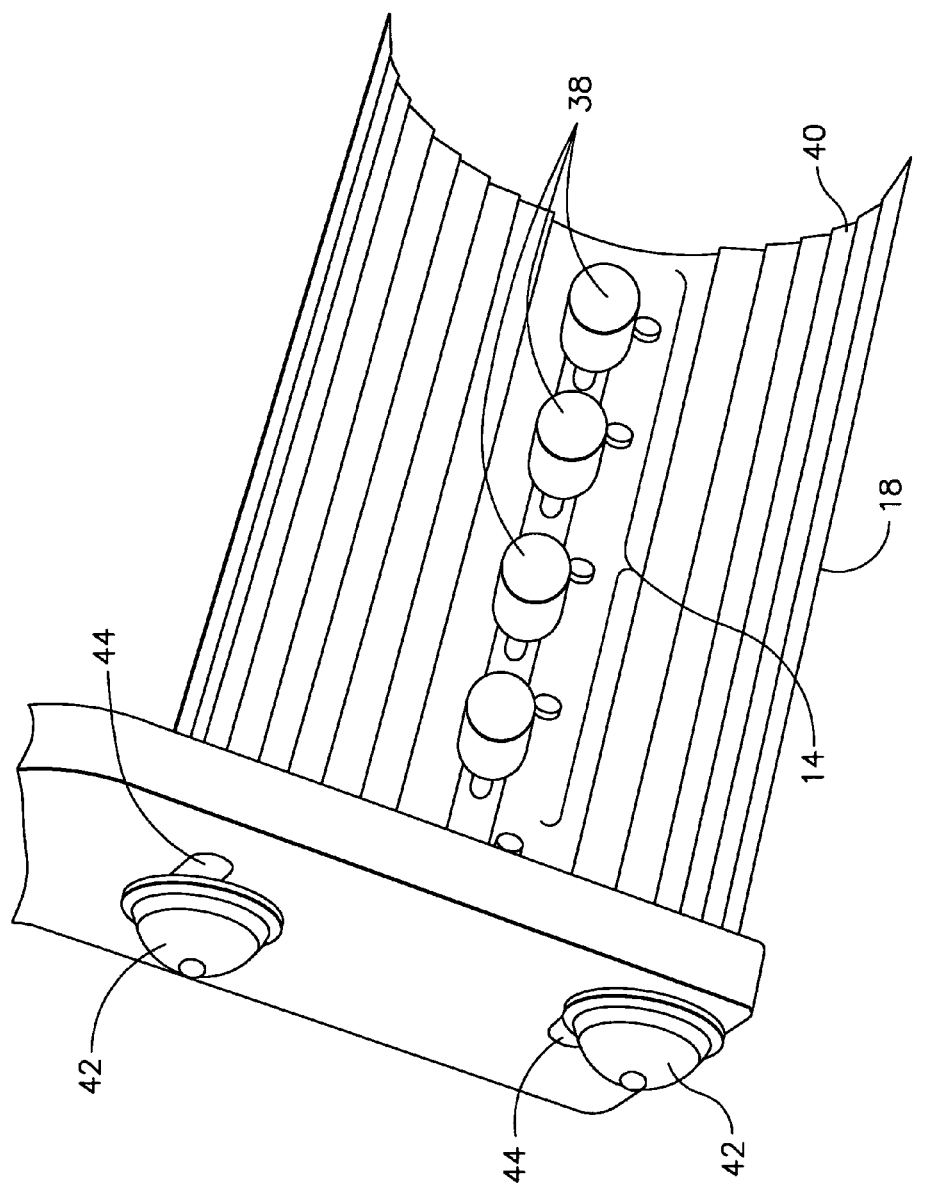
FIG. 3 is a perspective view of a light source according to the embodiment of the system shown in FIG. 2.

In another embodiment shown in FIGS. 2 and 3, the light source 14 includes four halogen light bulbs 38, although other quantities can also be used. To produce the dark field illumination for detecting FOD 21, one or more of the bulbs 38 are either deactivated/turned off or covered with an opaque material. In one embodiment, the bulbs 38 are coupled to a switching device that allows the operator to selectively activate and deactivate individual bulbs 38 and/or groups of the bulbs 38. The switching device can be implemented by conventional switches or by a control feature added to the user interface 76, described below.

Figure 5:
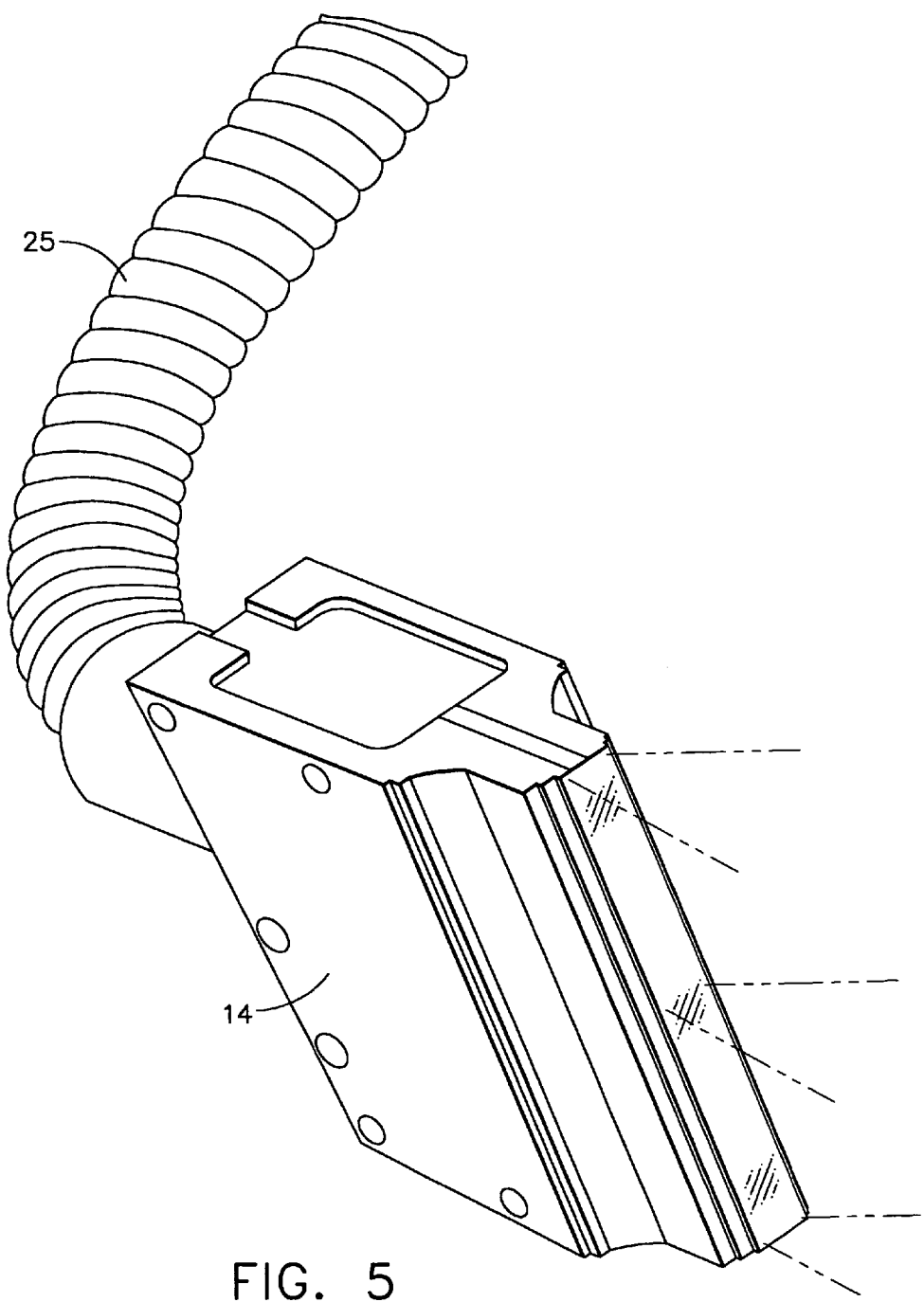
FIG. 5 is a perspective view of a light source according to the embodiment of the system shown in FIG. 4.

In the embodiment shown in FIG. 4, the light source 14 includes two linear optical fiber arrays positioned on opposite sides of the camera 12. The arrays emit light supplied from a remote source (not shown) through an optical fiber bundle 25. To produce the dark field illumination used in detecting FOD 21, a portion 35 of each array 14 is blocked or covered with an opaque material, which effectively shortens the array 14. In FIG. 5, there is shown a linear array 14 in which the portion 35 is not covered and the entire array is fully illuminated.

Referring back to FIG. 2, the system 10 may further include a light reflection element 18 located near the light source 14. The reflection element 18 include a series of light reflecting surfaces 40 (FIG. 3) that redirect the light towards the desired area to be illuminated. This levels the illumination across the surface and eliminates, or at least substantially reduce, areas of intense light (i.e., hotspots) created by the brightest portion of the light source 14. Hotspots are undesirable because hotspots prevent consistent illumination of the composite structure, which may lead to errors during the processing of the images captured by the camera 12.

The light reflection elements 40 are particularly advantageous for illuminating curved/contoured surfaces of composite structures because the redirection of the light permits a larger portion of the composite structure to be evenly illuminated.

As shown in FIG. 3, the reflection element 18 is curved around the light source 14, such as in a parabolic shape. On the surface of the reflection element 18 that faces the light source 14, the reflection element 18 includes curved steps 40 substantially parallel to the light source 14. The distance between and curvature of the steps 40 can be chosen to be sufficient to provide even illumination from the sum of the two light sources, one on either side of the region of interest. This enables the reflection element 18 to provide more consistent illumination of the composite structure 22, which prevents, or at least reduces, image processing errors due to inconsistent illumination of the composite structure 22. Alternatively, the shape and/or surface configuration of the reflection element 18 can be modified in other ways that also produce consistent illumination and scattering of the light produced by the light source 14 over the desired portion of the composite structure 22.

In an exemplary embodiment, the reflection element 18 has an overall parabolic shape with seventeen parabolic curved steps 40 having a range of widths from about 0.125 inches at the outer edge of the reflection element 18 to about 0.250 inches at the center of the reflection element 18. The reflection element 18 also has a uniform step height of about 0.116 inches. In other embodiments, however, the reflection element may be provided with different numbers of steps having different uniform or varying widths and different uniform or varying step heights.

Furthermore, the reflection element 18 may be adjusted in order to direct the light produced by the light source 14 and scattered by the reflection element 18 toward the desired portion of the composite structure. For example, as shown in FIG. 3, the reflection element 18 is adjustably mounted to the mounting apparatus 27 with fasteners 42. The loosened fasteners 42 can move within slots 44 to correspondingly adjust the angle of the reflection element 18 relative to the composite structure. Once the reflection element 18 is positioned appropriately, the fasteners 42 are tightened to secure the reflection element 18 in the desired position. Adjustments of the reflection element 18 can also be enabled by other methods, such as by electronic means that permit remote adjustment of the reflection element 18.

It has been observed that the composite structure 22 produces high glare when illuminated across the direction of placement of the strips 24 but produces substantially less glare when illuminated along the direction of placement of the strips 24. The systems and methods of at least some embodiments exploit the high-glare/low-glare phenomenon by casting light across the top layer of the composite strips 24 in a direction substantially perpendicular to the direction of placement of the strips 24. This produces a relatively large amount of glare on the top layer of the composite structure 22. The underlying layers, which produce significantly less glare than the top layer because of their orientation, will show through any gaps or other defects in the top layer and thus be easily located. In addition, twists and other surface defects in the top layer will alter the orientation of the strips in the top layer and thus correspondingly alter, i.e., decrease, the glare of the top layer at the defect location.

While the high-glare/low-glare phenomenon occurs when illuminated with either visible light or infrared light, the filter 15 used in one embodiment of the system 10 substantially removes the glare caused by ambient light such that only the glare caused by the infrared light source is used to locate the defects and FOD. Accordingly, the filter 15 removes the interference of ambient light as the composite structure 22 is being examined for defects and FOD.

In any of the system embodiments described herein, there may be one or more cameras 12 and/or one or more light sources 14 with or without reflection elements 18 (collectively referred to as light sources, hereinafter). In addition, the one or more cameras 12 and/or the one or more light sources 14 may be moveable relative to the composite structure. The multiple cameras 12 and/or multiple light sources 14 and the moveability of the camera(s) 12 and/or the light source(s) provides system 10 flexibility in order to capture the most accurate images of the composite structure. Multiple and/or moveable light source(s) 14 permit consistent and sufficient illumination of the desired portion of the composite structure, regardless of the shape of the composite structure. Likewise, multiple and/or moveable camera(s) 12 enable capturing an accurate image of any area of the composite structure, regardless of the shape of the composite structure. As such, the multiple and/or moveable light source(s) and/or camera(s) are particularly advantageous when illuminating and capturing images of and curved/contoured portions of composite structures. The multiple and/or moveable light source(s) and/or camera(s) are also advantageous in illuminating and capturing images of composite strips having a width that makes it difficult to illuminate and/or capture images of the entire strip, such that the position of the light source(s) and/or camera(s) may be moved over the entire strip, and/or multiple stationary light source(s) and/or camera(s) may be positioned to cover the entire strip. Systems including moveable cameras and light sources are described in detail in previously referred to U.S. patent application Ser. No. 10/217,805.

As shown in FIG. 1, the system 10 can also include a marking device 62 for marking the location of the defects and FOD on the composite structure 22. The marking device 62 may be attached to the frame 28 and be triggered by a processor 66 or similar device when a defect 36 or FOD 21 that is to be reported to the operator is detected. The marking device 62 may spray or otherwise deposit an amount of ink, paint or the like onto the composite structure 22 in those areas where defects 36 and FOD have been detected. The markings on the composite structure 22 enables the location of the defects and/or FOD to be subsequently readily identified either automatically or manually.

In the particular illustrated embodiment, the marking device 62 is an inkjet marking system that sprays a small spot of compatible ink of a highly visible color onto the surface of the composite structure 22 at the defect or FOD location to permit rapid access for repair and disposition. The marking device 62 may also be adapted to mark FOD with a different colored ink than that used to mark defects. Alternatively, other marking methods can also be used, such as a pump-fed felt-tip marker, spring-loaded marking pen, audio or visual alerts, and the like.

The automated collation process includes guiding the composite strips 24 (FIG. 1) from material creels (not shown) to an automated collation or fiber placement machine, such as a machine made by Cincinnati-Milacron and Ingersoll Milling Machines. In particular, the composite strips 24 are guided to a, head unit 23 (FIG. 3) and fed under a compaction roller 20. Focused heat energy is then applied to the incoming material and the underlying material that was previously laid to adhere the two materials. With the combination of pressure and heat, the composite strip 24 is consolidated into the previous layer, thus forming an additional layer of the composite structure 22. Unfortunately, defects 36 may sometimes occur during the placement of the composite strip 24 onto the underlying composite structure 22 and/or FOD may accumulate on a surface of the composite structure.

The camera 12 and/or the reflective surface 16, which along with the light source 14 and any reflection element 18, can be mounted to the head unit to allow the camera 12 to continuously capture real-time images of the composite structure 22 and the strips 24 as the head unit moves across the composite structure 22 and the composite strips 24 are laid down. If the composite structure 22 is not planar, the inspection point should be as close to the nip point as possible, as described above. If the composite structure 22 is planar, the inspection point can be located further from the placement head unit. In either case, the images can be stored in a memory device 64 for future analysis and/or processed immediately by the processor 66, as discussed more fully below.

Figure 6:
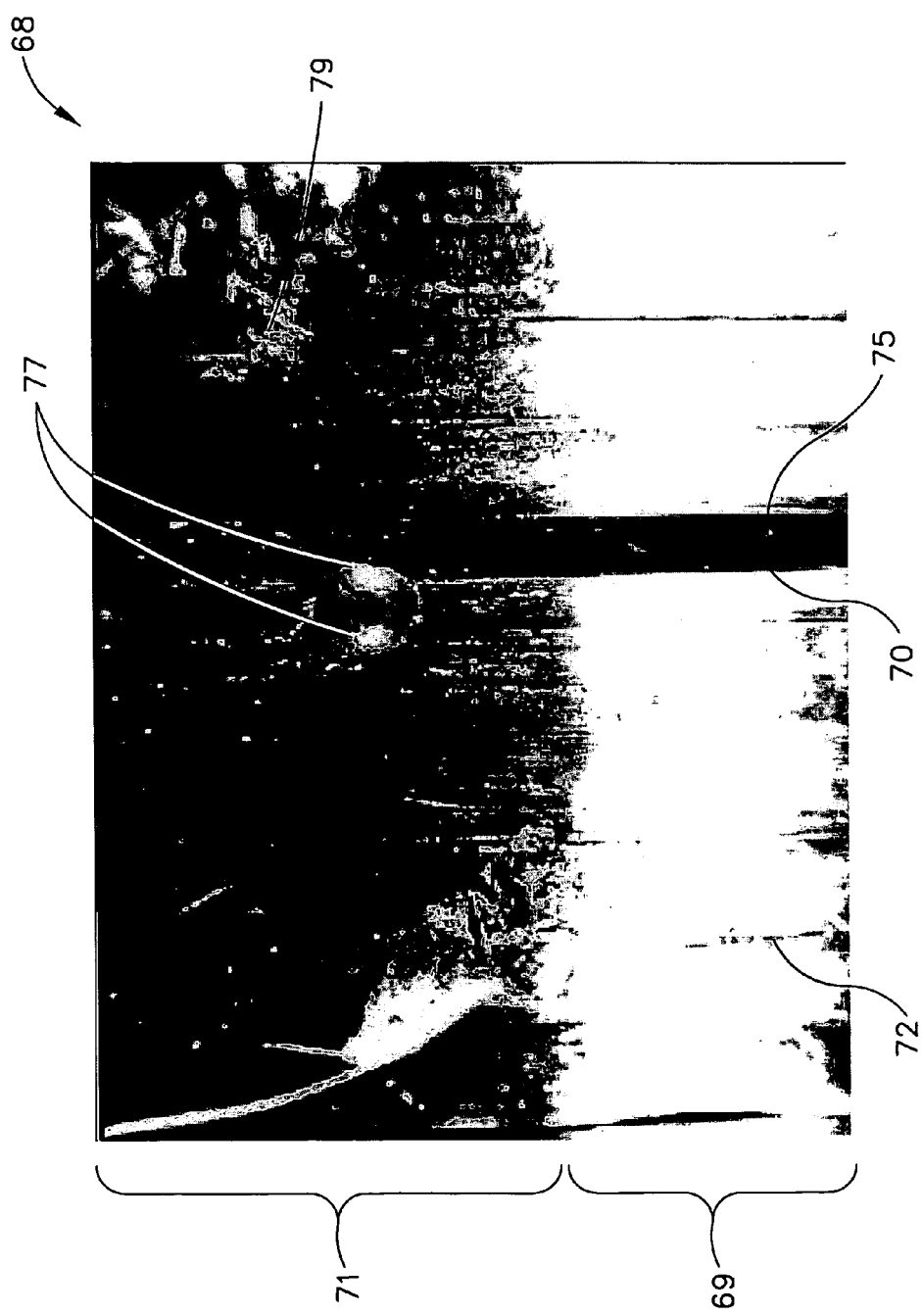
FIG. 6 is a video frame capturing both FOD and a gap between tows as captured by one embodiment of the present invention.

FIG. 6 shows an exemplary raw or unprocessed camera image 68, which includes a plurality of pixels having a range from black through a plurality of shades of gray to white. The image 68 includes a bright field 69 and a dark field 71. The bright field 69 corresponds to the first portion 17 (FIG. 1) of the composite structure illuminated with the bright field illumination, whereas the dark field 71 corresponds to the second portion 19 (FIG. 1) illuminated with the dark field illumination.

The bright field 69 in the unprocessed camera image 68 illustrates a contrast between a potential defect 75, such as a tow gap, and the remaining portions of the composite structure 22 that are defect free. In the illustrated embodiment of the bright field 69, the potential defects are shown as black or gray areas 70, while the remaining non-defective portions of the composite structure 22 remain substantially white 72. Once the potential defects are located, however, the potential defects may still require further processing to determine if the potential defects are acceptable or unacceptable, as described below.

The dark field 71 of the unprocessed camera image 68 illustrates a contrast between the dark field illumination that is reflected by FOD and the remaining portions of the composite structure 22 that are FOD free. In the illustrated embodiment of the dark field 71, a resin ball is indicated by way of two substantially white reflection spots 77 visible on either side of the resin ball. A potential fuzz ball is shown as a substantially white area 79 indicative of the dark field illumination being reflected from the edges and fiber ends of the fuzz ball. The remaining FOD-free portions of the composite structure 22 remain black or gray.

Although resin balls and fuzz balls are visually different in the image 68, further processing may still be required to differentiate the resin balls from the fuzz balls, for example, to allow the marking device 62 (FIG. 1) to mark resin balls with a different colored ink than that used to mark fuzz balls. To differentiate resin balls from fuzz balls, a known "blob" imaging process can be used in which a series of decisions are made based upon mathematical operations and comparisons to established criteria for specific geometries. One differentiator that can be used to distinguish between resin balls and fuzz balls is edge roughness because fuzz balls have greater edge roughness than resin balls.

Further processing may also be needed to determine whether a potential FOD anomaly is acceptable or unacceptable according to maximum allowable dimensional parameters. That is, the system may only mark or flag FOD which exceed the maximum allowable dimensional parameters. To make this determination, the system may count the number of pixels within a particular image region that represents the reflected dark field illumination by a potential FOD anomaly. The system may then use the pixel count to compute an indirect quantitative measurement for the particular FOD anomaly based upon correlation data including a predetermined relationship between pixel count and FOD size.

With further reference to FIG. 1, the processor 66 may receive the images 68 from the camera 12 or from the memory device 64 in which the images 68 have been stored. The processor 66 may then process and analyze the images to facilitate the reliable detection of defects and FOD. In at least one embodiment, the processor 66 and memory device 64 are components of a conventional computer.

The system 10 may also includes a user interface 76 that is in communication with the processor 66. The user interface 76 can be programmed such that it can run from a wide range of software applications, including but not limited to DOS, Windows 98, Windows/NT, Windows 2000, Windows CE, Linux, Unix, and equivalents.

Figure 7:
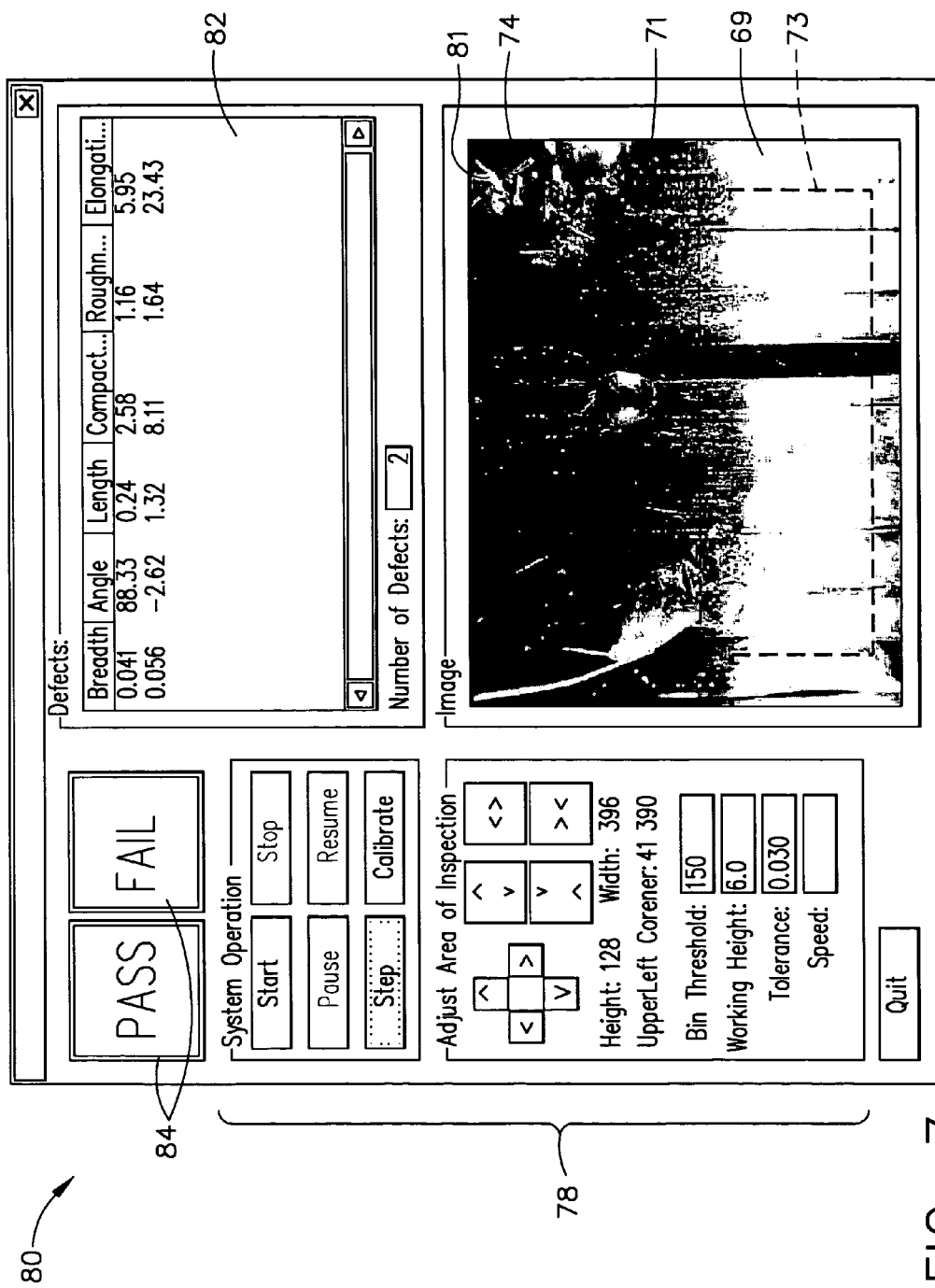
FIG. 7 is a view of a computer display and selected user controls according to one embodiment of the present invention.

As shown in FIG. 7, the user interface 76 includes a display screen 80, such as on a computer monitor, and can also include an input device, such as a keyboard and mouse (not shown), for permitting an operator to move a cursor about the display screen 80 and input various system settings and parameters. The display screen 80 can also be touch-sensitive for permitting the operator to input the desired settings by manually touching regions of the display screen.

The user interface 76 includes a window 81 in which an image 74 of the composite structure 22 is displayed for viewing by the operator or other user. Although the image 74 can be the unprocessed camera image 68 (FIG. 6), the image 74 shown in FIG. 7 is a processed image in which the rectangular region 73 has been binarized. During binarization, all shades of gray above a predetermined threshold value can be changed to white, while all gray shades below the threshold are changed to black to heighten the contrast of defects and improve the accuracy of defect detection. In other embodiments, the binarization step need not be performed but instead the raw image, rates of change of the light levels in the raw image, and/or color changes in the images can be used to identify the defects and FOD.

The user interface 76 also provides user controls 78 for allowing various user inputs to the system. In the particular illustrated embodiment of FIG. 7, the user interface 76 allows adjustment to the binarization threshold. Generally, the setting of the binarization threshold involves a tradeoff between the sensitivity with which defects are detected and the resolution with which the defects are depicted. In one embodiment, the binarization threshold is set to about 128 which corresponds to the mid-point on the 8-bit digitizing range of 0 to 255. However, other binarization threshold values can be employed depending at least in part on the particular application, available lighting, camera settings, among other factors.

The user controls 78 also allow the user to adjust or shift the viewing area within the window 81. During operation, the window 81 displays real-time moving video images of the illuminated portions 17 and 19 of the composite structure 22 as the camera 12 and/or the reflective surface 18 are moved relative to the composite structure 22. By accessing the user controls 78, the user can shift or adjust the window 81 such that the window 81 simultaneously displays both the bright field 69 and the dark field 71.

The interface 76 may also allow the user to input the maximum allowable dimensional parameters for acceptable defects and FOD and/or input the acceptable tolerances of the maximum dimensional parameters, among others.

In addition to displaying images of the composite structure 22, the display screen 80 also includes a defect table 82 which lists the discovered defects and provides information for each defect, such as location, size, and the like. The display screen 80 can also include an FOD table (not shown) for listing and providing information about the discovered FOD anomalies. The display screen 80 can further include status indicators 84 that notify the user whether a particular image area is acceptable or not acceptable based on pre-defined criteria, such as maximum allowable dimensional parameters and tolerances.

Figure 8:
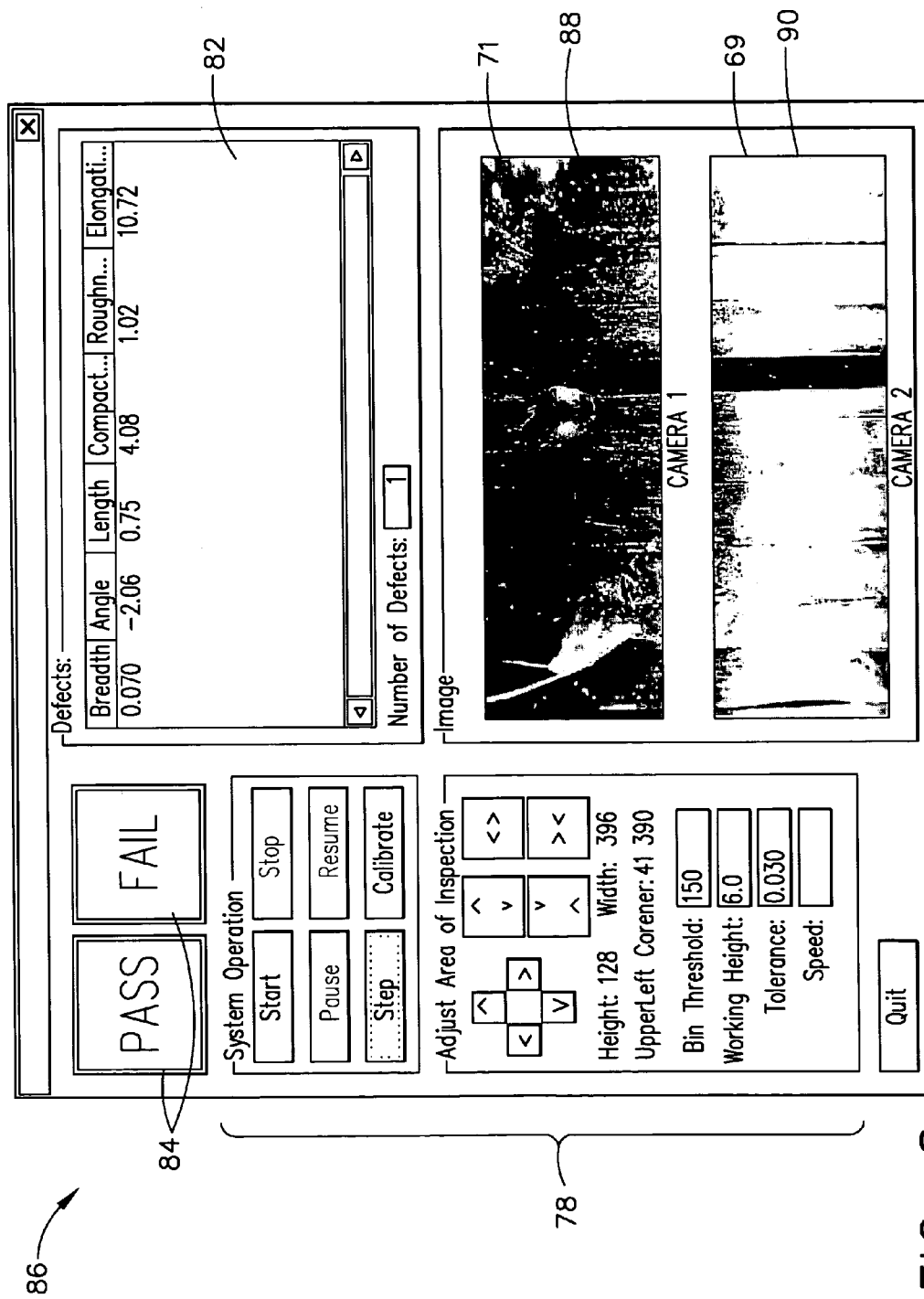
FIG. 8 is a view of a computer display and selected user controls according to another embodiment of the present invention.

FIG. 8 illustrates another embodiment of the user interface 76 that may be used in a system 10 that includes two or more cameras 12 for capturing images of the composite structure 22. As shown, the user interface 76 includes a display screen 86 that displays images 88 and 90 of the composite structure 22 for viewing by the operator or other user. The image 88 is captured by the first camera and represents the portion 17 of the composite structure 22 illuminated with bright field illumination. The dark field image 90 is captured by the second camera and represents the portion 19 of the composite structure 22 illuminated with dark field illumination. Alternatively, multiple user interfaces can be used to display the images of multiple cameras 12 in which each interface displays an image from one or more cameras and presents one or more links to the user interface(s) that display images from the other camera(s). Images from multiple cameras mounted side by side can be assembled to form a composite view of a larger area of the composite structure.

In another form, the present invention provides methods for identifying FOD and defects during fabrication of a composite structure. In one embodiment, the method generally comprises: illuminating a portion of the composite structure with bright field illumination; illuminating another portion of the composite structure with dark field illumination; acquiring an image of the illuminated portions of the composite structure; analyzing the image to identify defects in the portion of the composite structure illuminated by bright field illumination; and analyzing the image to identify foreign objects and debris on the another portion of the composite structure illuminated by dark field illumination.

Accordingly, embodiments of the present invention can operate more efficiently with fewer interruptions than conventional fiber placement systems because human intervention is not required for inspection of the composite structure for defects and foreign objects and debris (FOD). Instead, the embodiments of the present invention can rapidly detect and identify defects and FOD so that the same can be subsequently readily identified during remedial actions to repair the defects and/or remove the FOD, which would otherwise create structural flaws or inconsistencies that may affect the integrity of the composite structure. As such, less material is wasted, less labor is expended in inspection, and less machine downtime is incurred during the fabrication process; therefore, a lower cost composite structure is achieved on average. Additionally, embodiments also enable an improvement in the overall quality of the parts produced because defects and FOD can be detected more uniformly and reliably with the various automated systems and methods of the invention than a traditional human inspection.

The description of the invention is merely exemplary in nature and is in no way intended to limit the invention, its application, or uses. Thus, variations that do not depart from the substance of the invention are intended to be within the scope of the invention. Such variations are not to be regarded as a departure from the spirit and scope of the invention.

What is claimed is:

1. A system for identifying defects and foreign objects and debris during fabrication of a composite structure, the system comprising:

at least one light source positioned to emit light for illuminating a portion of the composite structure with bright field illumination and another portion of the composite structure with dark field illumination, the bright field illumination being reflected differently by defects in the composite structure than from portions of the composite structure that are defect free, the dark field illumination being reflected differently by foreign objects and debris on the composite structure than from surfaces of the composite structure not having foreign objects and debris thereon;

at least one camera for receiving images of the illuminated portions of the composite structure;

the composite structure includes a plurality of adjacent composite strips positioned in a common direction; and the light source is positioned to emit light in a direction substantially perpendicular to the common direction of the composite strips.

2. The system of claim 1, further comprising a processor for processing the images and outputting a response identifying defects and foreign objects and debris based on the images.

3. The system of claim 2, further comprising an interface for allowing at least one user input for the processor.

4. The system of claim 3, wherein:

the processor is capable of binarizing images by setting all pixels representing a color darker than a predetermined gray level to one of black or white and setting all other pixels to the other of black or white; and the user interface allows a user to set a threshold representative of the predetermined gray level utilized by the processor to binarize the images.

5. The system of claim 1, further comprising a memory device for storing the images.

6. The system of claim 1, wherein the light source is moveable relative to the composite structure.

7. The system of claim 1, wherein the at least one light source comprises a plurality of light sources located at different respective positions relative to the composite structure.

8. The system of claim 1, wherein the at least one light source comprises a plurality of light sources coupled to a switching device for selectively activating and deactivating the light sources.

9. The system of claim 8, wherein the switching device comprises a user interface.

10. The system of claim 1, wherein:
the camera is moveable relative to the composite structure; and
the camera receives real-time images of the illuminated portions of the composite structure as the camera moves relative to the composite structure.

11. The system of claim 1, wherein the camera and the light source are mounted on a head unit of a fiber placement machine.

12. The system of claim 1, wherein the at least one camera comprises:
a first camera for receiving images of the portion of the composite structure being illuminated by bright field illumination; and
a second camera for receiving images of the portion of the composite structure being illuminated by dark field illumination.

13. The system of claim 1, further comprising at least one reflective surface proximate the composite structure such that the camera receives the images of the illuminated portions following reflection of the images from the reflective surface.

14. The system of claim 12, wherein the reflective surface and the light source are mounted on a head unit of a fiber placement machine.

15. The system of claim 1, wherein the camera comprises at least one of:
an infrared-sensitive camera; and
a visible light camera with infrared-pass filtration.

16. The system of claim 1, further comprising a filter for preventing substantially all ambient visible light from entering the camera.

17. The system of claim 1, wherein the camera is capable of distinguishing light from the light source and ambient visible light.

18. The system of claim 1, further comprising a light reflection element proximate the light source to redirect light from the light source towards the composite structure.

19. The system of claim 1, wherein the light source includes an infrared component.

20. The system of claim 1, wherein the light source comprises at least one of:
an incandescent light;
a light emitting diode;
a noble gas arc lamp;
a metal arc lamp;
a strobe;
a fluorescent light; and
a laser.

21. The system of claim 1, further comprising a marking device for marking the defects and foreign objects and debris identified by the system.

22. The system of claim 21, wherein the marking device comprises at least one of an inkjet sprayer and a pump-fed felt-tip marker.

23. A system for identifying defects and foreign objects and debris during fabrication of a composite structure, the system comprising:
at least one light source positioned to emit light for illuminating a portion of the composite structure with bright field illumination and another portion of the composite structure with dark field illumination, the bright field illumination being reflected differently by defects in the composite structure than from portions of the composite structure that are defect free, the dark field illumination being reflected differently by foreign objects and debris on the composite structure than from surfaces of the composite structure not having foreign objects and debris thereon;
at least one camera for receiving images of the illuminated portions of the composite structure;
wherein the camera and the light source are mounted on a head unit of a fiber placement machine;
wherein the camera receives real-time images of the illuminated portions of the composite structure as the head unit moves across the composite structure.

24. A system for identifying defects and foreign objects and debris during fabrication of a composite structure, the system comprising:
at least one light source positioned to emit light for illuminating a portion of the composite structure with bright field illumination and another portion of the composite structure with dark field illumination, the bright field illumination being reflected differently by defects in the composite structure than from portions of the composite structure that are defect free, the dark field illumination being reflected differently by foreign objects and debris on the composite structure than from surfaces of the composite structure not having foreign objects and debris thereon;
at least one camera for receiving images of the illuminated portions of the composite structure;
wherein the camera and the light source are proximate a compaction roller of a fiber placement machine.

25. A system for identifying defects and foreign objects and debris during fabrication of a composite structure, the system comprising:
at least one light source positioned to emit light for illuminating a portion of the composite structure with bright field illumination and another portion of the composite structure with dark field illumination, the bright field illumination being reflected differently by defects in the composite structure than from portions of the composite structure that are defect free, the dark field illumination being reflected differently by foreign objects and debris on the composite structure than from surfaces of the composite structure not having foreign objects and debris thereon;
at least one camera for receiving images of the illuminated portions of the composite structure;
at least one reflective surface proximate the composite structure such that the camera receives the images of the illuminated portions following reflection of the images from the reflective surface;
wherein the reflective surface and the light source are proximate a compaction roller of a fiber placement machine.

26. A system for identifying defects and foreign objects and debris during fabrication of a composite structure, the system comprising:
at least one light source positioned to emit light for illuminating a portion of the composite structure with bright field illumination and another portion of the composite structure with dark field illumination, the bright field illumination being reflected differently by defects in the composite structure than from portions of the composite structure that are defect free, the dark field illumination being reflected differently by foreign objects and debris on the composite structure than from surfaces of the composite structure not having foreign objects and debris thereon:
- at least one camera for receiving images of the illuminated portions of the composite structure;
- a light reflection element proximate the light source to redirect light from the light source towards the composite structure;
- wherein the light reflection element comprises a plurality of reflective parabolic curved surfaces in a stepped configuration.

27. The system of claim 23, further comprising a processor for processing the images and outputting a response identifying foreign objects and debris based on the images.

28. A method for identifying defects and foreign objects and debris during fabrication of a composite structure, the method comprising:
- illuminating a portion of the composite structure with bright field illumination that is reflected differently by defects in the composite structure than from portions of the composite structure that are defect free;
- illuminating another portion of the composite structure with dark field illumination that is reflected differently by foreign objects and debris on the composite structure than from surfaces of the composite structure not having foreign objects and debris thereon;
- acquiring an image of the illuminated portions of the composite structure;
- analyzing the image to identify defects in the portion of the composite structure illuminated by the bright field illumination;
- analyzing the image to identify foreign objects and debris on the another portion of the composite structure illuminated by the dark field illumination; and
- positioning at least one light source to emit light for illuminating the portion of the composite structure with bright field illumination while also illuminating the another portion of the composite structure with dark field illumination.

29. The method of claim 28, wherein:
- analyzing the image to identify defects comprises analyzing image portions representative of reflections of the bright field illumination; and
- analyzing the image to identify foreign objects and debris comprises analyzing image portions representative of reflections of the dark field illumination.

30. The method of claim 28, wherein analyzing the image to identify defects comprises converting at least a portion of the image into a dichotomous representation above or below a threshold.

31. The method of claim 28, further comprising marking defects and foreign objects and debris on the composite structure.

32. The method of claim 28, further comprising moving the light source relative to the composite structure to illuminate other portions of the composite structure with bright field illumination and dark field illumination.

33. The method of claim 32, further comprising moving a camera relative to the composite structure to acquire images with the camera of the other illuminated portions.

* * * * *